HACKBERRY TREE
Filed June 27, 1974 2 Sheets-Sheet 1
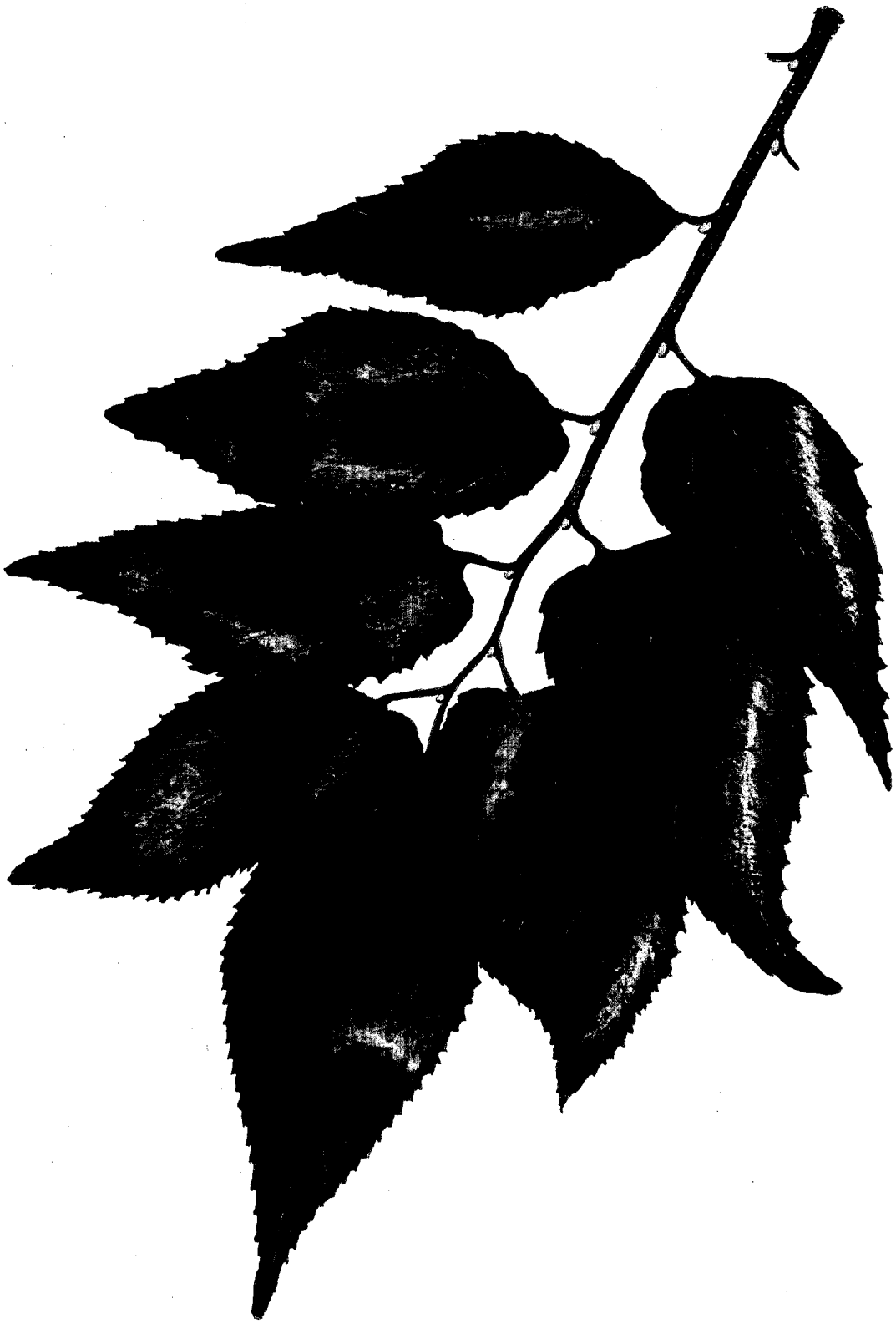

HACKBERRY TREE
Filed June 27, 1974 2 Sheets-Sheet 2
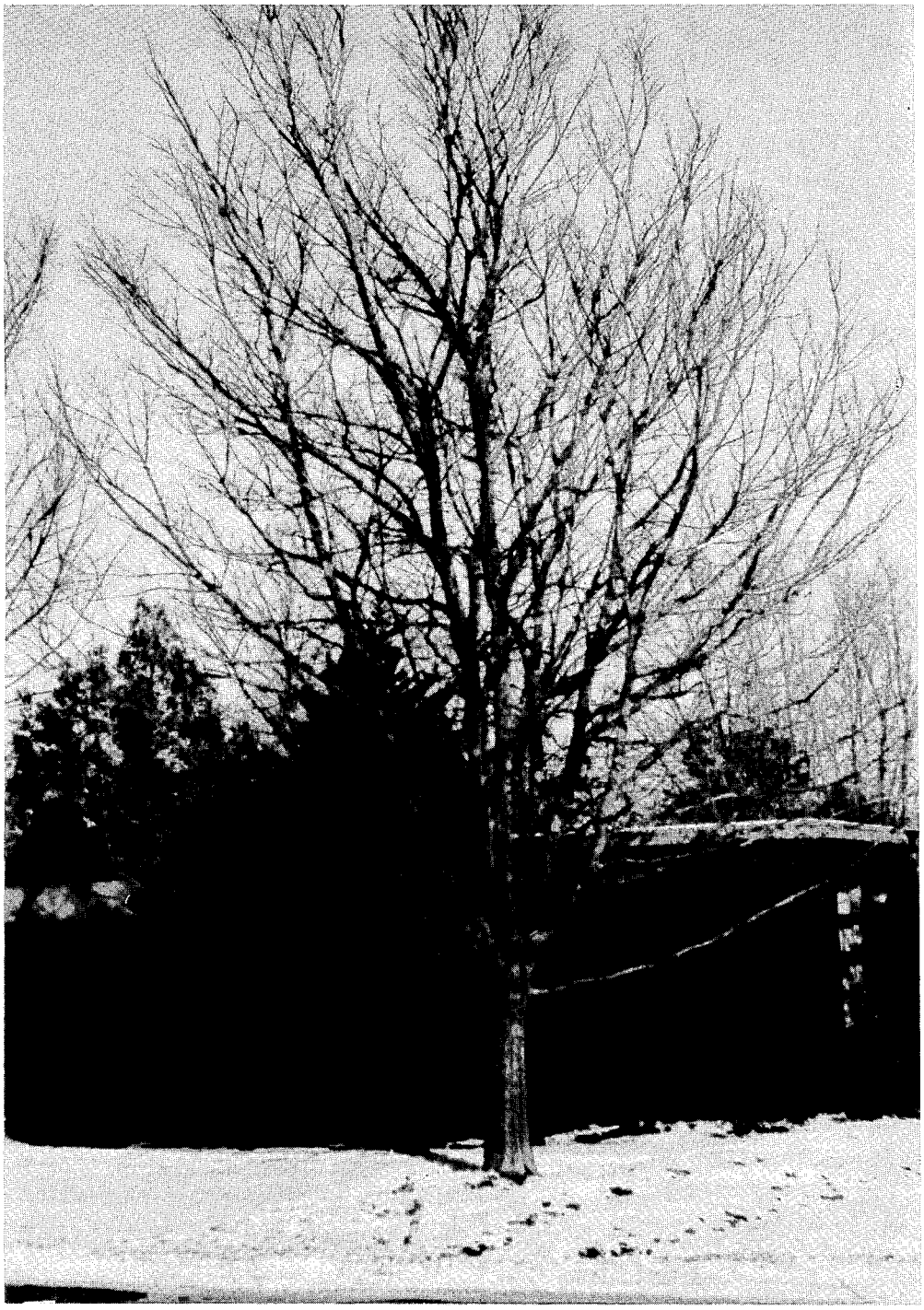

United States Patent

Plant Pat. 3,771
Patented Aug. 26, 1975

3,771

HACKBERRY TREE

Willet N. Wandell, Rte. 3, Myra Station Road,
Urbana, Ill. 61801

Filed June 27, 1974, Ser. No. 483,886
Int. Cl. A01h 5/12
U.S. Cl. Plt.—51 1 Claim This invention relates to a new and distinct variety of a hackberry tree which was discovered in a growth of *Celtis occidentalis,* in Urbana, Ill.

The new and distinct variety of hackberry tree has characterizations which renders such new variety vastly different from the other hackberry trees grown in Urbana, Ill. The new variety was discovered from a seedling source by noting the vast differences in growth habits.

The unique combination of characteristics in the new hackberry tree variety includes dark green foliage and lustrous upper surface of the leaves, as well as a tight compact habit of growth with a spreading rounded crown relatively low in profile and less towering than other observed hackberries.

The new variety has been asexually reproduced by obtaining bud wood for propagation. The tree reproduced readily from budding, and whips were produced in propagation that grew upright and were relatively free of the many side branches which are frequently encountered in first year whips of this species produced by budding.

The primary object of the present invention is therefore to provide a new and distinct hackberry tree variety having the desirable characteristics referred to above and to be described in detail below. Other objects and advantages of the invention will become apparent from the following detailed description when taken together with the accompanying illustrations, in which:

FIG. 1 illustrates a denuded tree after about ten growing seasons; and

FIG. 2 is a color illustration of the foliage.

The color references used herein relate to the Royal Horticultural Colour Chart, published by the Royal Horticultural Society of London, Library Calling No. 581.4, B 77. The physical characteristics of the new variety may be summarized as including a low spreading growth habit unlike many hackberries observed which show a vase shape, towering habit of growth; the heavy green leaves which are slightly more glossy than most hackberries; and an outstanding ability to reproduce by budding.

The new variety is obtained from an unnamed seedling of the species *Celtis occidentalis.* The new variety reproduces readily and well without superfluous branching habit of first year whips such as shown in many other hackberry selections. The new variety was grown and observed in Urbana, Ill. The tree is dense, has a rounded crown, is characterized by spreading, and is hardy.

The trunk is characterized by a grayish color, said trunk being rough with corky warts or ridges.

The branches are characterized by being slender and following a zig-zag pattern. The branches are pubescent when young but soon become glabrous. The color of the branches is a light olive green, color No. 138B. The lenticles are prominent and numerous.

The foliage is characterized by leaves which are of simple configuration, having a length from 5 to 12 cm. and a width from 3 to 5.5 cm. The shape of the leaves is ovate to oblong-ovate. The apex of the leaves is acute to acuminate. The base of the leaves is oblique and rounded to obliquely auriculate. The margin of the leaves is serrate, except at the base. The color of the leaves is a lustrous dark green above, No. 139A, and dull green beneath, No. 147B. The leaves have a velvety pubescence when young and are glabrous or nearly so when mature or slightly hairy on the veins beneath. The petiole is from about 1 to 1.5 cm. long, and slightly pubescent.

No flowers or flower buds have been observed.

The hackberry illustrated in FIG. 1 attains a height of about 8 ft. after ten growing seasons.

What is claimed is:

1. A new and distinct variety of hackberry substantially as described and illustrated herein, characterized particularly by low spreading habit of growth, heavy dark green leaves of increased glossy character, and reproduction from buds of whips which show few superfluous side branches.

No references cited.

ROBERT E. BAGWILL, Primary Examiner